United States Patent
Dettinger et al.

(10) Patent No.: US 8,495,084 B2
(45) Date of Patent: Jul. 23, 2013

(54) MOLECULAR LEVEL SIMILARITY SEARCH AND COMPUTER AIDED DRUG DISCOVERY PROCESS

(75) Inventors: Richard D. Dettinger, Rochester, MN (US); Barry Robson, Grand Cayman (KY)

(73) Assignee: International Business Machines Corporation, Armonk, NY (US)

( * ) Notice: Subject to any disclaimer, the term of this patent is extended or adjusted under 35 U.S.C. 154(b) by 716 days.

(21) Appl. No.: 12/560,748

(22) Filed: Sep. 16, 2009

(65) Prior Publication Data

US 2011/0066632 A1    Mar. 17, 2011

(51) Int. Cl.
*G06F 17/30* (2006.01)
(52) U.S. Cl.
CPC ............................... *G06F 17/30017* (2013.01)
USPC ........................................................ 707/769
(58) Field of Classification Search
USPC ................ 707/606, 707, 729, 731, 769, 770; 514/252.1, 293
See application file for complete search history.

(56) References Cited

U.S. PATENT DOCUMENTS

| | | | | |
|---|---|---|---|---|
| 5,577,239 | A * | 11/1996 | Moore et al. | 707/752 |
| 6,304,869 | B1 * | 10/2001 | Moore et al. | 1/1 |
| 2007/0016612 | A1 * | 1/2007 | James et al. | 707/104.1 |

OTHER PUBLICATIONS

David Weininger, SMILES, a Chemical Language and Information System, Jun. 17, 1987, Google, 31-36.*
H. Wang et al., An Approach in Building a Chemical Compound Search Engine in Oracle Database, Sep. 2005, IEEE, 2839-2842.*

* cited by examiner

*Primary Examiner* — Jean B Fleurantin
(74) *Attorney, Agent, or Firm* — Patterson & Sheridan LLP

(57) ABSTRACT

Systems, methods and articles of manufacture are disclosed for searching chemical compounds referenced in chemical literature. References to chemical compounds in the documents may be transformed to corresponding references using a standard notation for representing chemical compounds. Criteria specifying desired molecular characteristics may be received. A regular expression may be generated based on the received criteria. The chemical documents may be searched using the regular expression. Based on the search, a chemical document may be determined that references a chemical compound satisfying the received criteria. Further, the regular expression may be generated based on the received criteria and a received mutation rule. Based on the generated regular expression and the chemical documents, one or more chemical compounds may be discovered that satisfy both the received criteria and the received mutation rule, but that is are not referenced in the chemical documents.

15 Claims, 8 Drawing Sheets

300
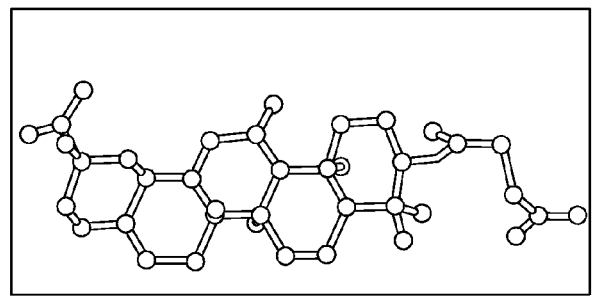
302
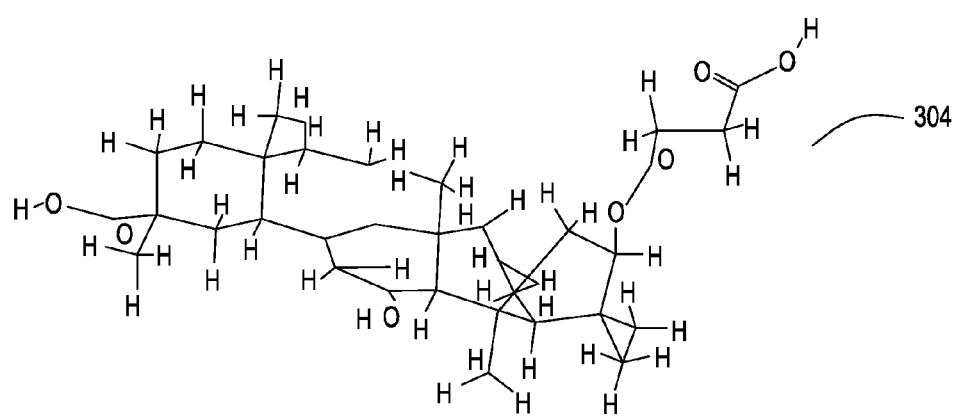
304
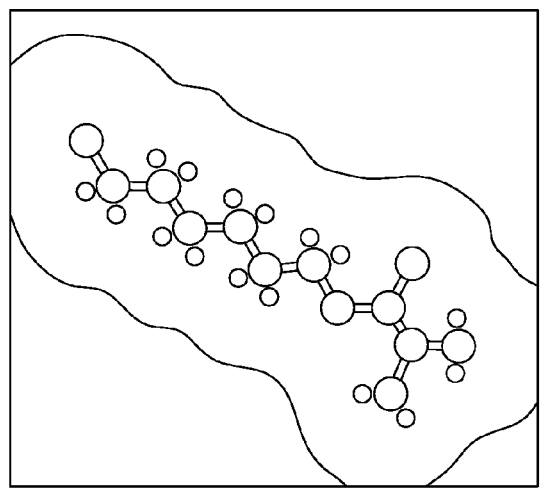
306
FIG. 3

| Iteration | Hits | Regular Expression |
|---|---|---|
| 1 | 1 | C\(\[C\(\[C@\]@\)\]\1(C)\[C@@\]2(\[H\])C3=CC\(=O\)\[C@\]4(\[C@\]\(CCC5\[C@@\]4(CC\(\[C@H\]\(O_C\(C\)5C\)... |
| 2 | 0 | \)\(C\[C@@\]\)C\(\(\[*O\]+\)\)?C\[C@@\]\)D\(C\)\)CD=C\(\[H\]\)CD\(\[C@@\]\)D\(C\(\[C@H\]\)\(O\)\(C\)\)DC\(\[OC\(=O...) |
| 3 | 0 | \)\(C\[C@@\]\)C\(\(\[*O\]+\)\)?C\[C@@\]\)D\(C\)\)D\(C\)\)D\(C\)\)?CD\(C\(\[*O\]+\)\)?C\(\[C@H\]\(S\)\)C\(C\)\)DC\)O |
| 4 | 0 | \)\(C\[C@@\]\)C\(\(\[*O\]+\)\)?C\(=S\)\)C\(\[*O\]+\)\)?CD\[C@@\]\)D\(C\)\)?CD\[C@@\]\)?C\(\[C@H\]\(S\)\)C\(C\)\)DC\)O |
| 5 | 1 | C\(\[C@@\]@\)\)CC\[C@@\]\)\1(C)\[C@@\]2(\[H\])C3=CC\(=O\)\[C@\]4(\[C@@H\]\(O_C\(C\)5C\)... |
| 6 | 0 | \)\(C\[C@@\]\)C\(\(\[*O\]+\)\)?C\(=S\)\)C\(\[C@@\]\)D\(C\(\[C@H\]\)\(CCD\[C@@\]\)D\(C\)\)?CD\[C@@\]\)?C\(\[C@H\]\(O\)\(C\)\)DC\(\[OC\(=O |
| 7 | 0 | \)\(C\[C@@\]\)C\(\(\[*O\]+\)\)?C\(=S\)\)C\(\[C@@\]\)D\(C\)\)?CD\[C@@\]\)D\(C\)\)?CD\[C@@\]\)?C\(\[C@H\]\(S\)\)C\(C\)\)DC\)O |
| 8 | 0 | \)\(C\[C@@\]\)C\(\(\[*O\]+\)\)?C\(=S\)\)C\(\[C@@\]\)D\(C\(\[C@H\]\)\)CD\[C@@\]\)D\(C\(\[C@@\]\)?C\(\[C@H\]\(S\)\)C\(C\)\)DC\)O |

MOLECULAR LEVEL SIMILARITY SEARCH AND COMPUTER AIDED DRUG DISCOVERY PROCESS

BACKGROUND OF THE INVENTION

1. Field of the Invention

Embodiments of the invention relate to searching chemicals referenced in chemical literature. More specifically, embodiments of the invention relate to a molecular level similarity search process and computer aided drug discovery process.

2. Description of the Related Art

A variety of chemical literature sources include references to chemical compounds and molecules. The references express the chemical structure for compounds in a variety of ways. For example, a chemical research paper may include a reference to hexane (an alkane hydrocarbon). Alternatively, the chemical research paper may include a reference to $C_6H_{14}$ (i.e., a molecular formula for hexane), $CH_3CH_2CH_2CH_2CH_2CH_3$ (a structural formula for hexane), $CH_3(CH_2)_4CH_3$ (a structural formula for hexane), $C_3H_7$ (an empirical formula for hexane), etc. That is, literature sources may refer to a compound or molecule using a variety of distinct names and formulas, some of which are long and complex.

SUMMARY OF THE INVENTION

One embodiment of the invention includes a computer-implemented method. The computer-implemented method includes configuring one or more computer processors to perform an operation for searching a plurality of documents which include references to chemical compounds. The operation may generally include receiving the plurality of documents; receiving criteria specifying desired chemical characteristics; generating at least one regular expression based on the received criteria; evaluating, by operation of the one or more computer processors, chemical compounds referenced in the plurality of documents against the regular expression to identify, one or more of the plurality of documents that reference a chemical compound satisfying the received criteria.

Another embodiment of the invention includes a computer-readable storage medium containing a program, which when executed by the processor is configured to perform an operation for searching a plurality of documents which include references to chemical compounds. The operation may generally include receiving the plurality of documents; receiving criteria specifying desired chemical characteristics; generating at least one regular expression based on the received criteria; evaluating chemical compounds referenced in the plurality of documents against the regular expression to identify, one or more of the plurality of documents that reference a chemical compound satisfying the received criteria.

Still another embodiment of the invention includes a system having a processor and a memory containing a program, which when executed by the computer processor is configured to perform an operation for searching a plurality of documents which include references to chemical compounds. The operation may generally include receiving the plurality of documents; receiving criteria specifying desired chemical characteristics; generating at least one regular expression based on the received criteria; evaluating, by operation of the computer processor, chemical compounds referenced in the plurality of documents against the regular expression to identify, one or more of the plurality of documents that reference a chemical compound satisfying the received criteria.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 3 illustrates GUI screens for assisting a user in specifying criteria that specify desired chemical characteristics, according to one embodiment of the invention.

FIG. 4 illustrates a GUI output of a search tool, according to one embodiment.

DETAILED DESCRIPTION OF THE PREFERRED EMBODIMENTS

Figure 1:
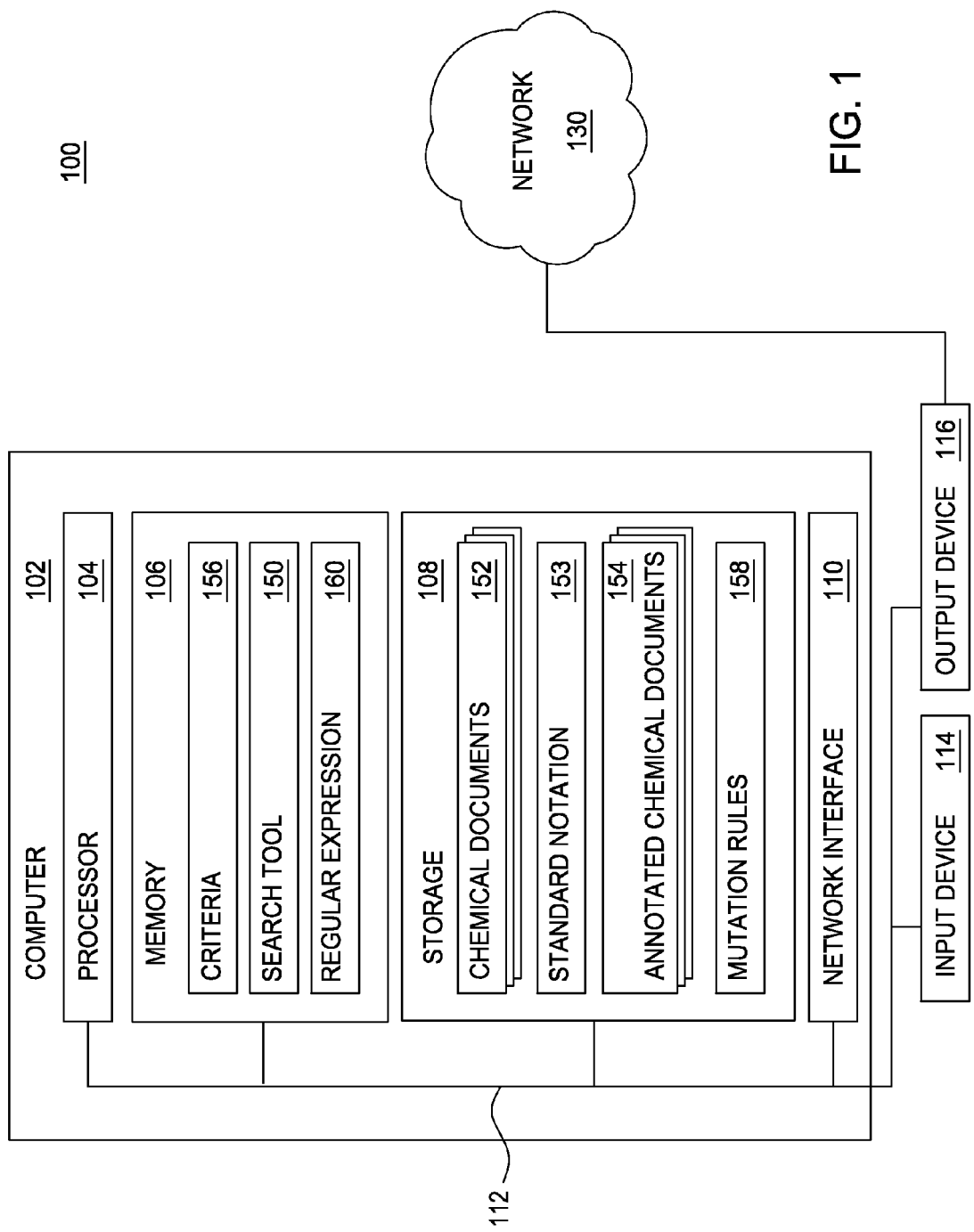
FIG. 1 is a block diagram illustrating a system for searching chemicals referenced in chemical documents, according to one embodiment of the invention.

Embodiments of the present invention generally query for references to chemicals (i.e., compounds and molecules) in chemical literature. The chemical literature may include a plurality of documents (e.g., research papers, patents, lab experiment reports, etc.). A reference to a single compound or molecule may be expressed in variety of distinct ways (e.g., different scientific names and formulas for the same compound or molecule). Further, many of the references may be long and complex. While the references may be understood by people with chemistry backgrounds, the lack of a single naming scheme prohibits searching effectively for a desired compound or molecule.

One embodiment of the invention provides a standard notation for representing a chemical compound or molecule. Further, one embodiment of the invention provides an application program executed on a computer. The application program, referred to as a search tool, may receive the chemical literature. Further, the search tool may convert the chemical literature into a standard notation. For example, the search tool may annotate the chemical literature using the standard notation. For instance, each reference in the chemical literature to a compound or molecule may be annotated with a standard notation for representing the compound or molecule. As a further example, the search tool may generate an annotated index to chemicals referenced in the chemical literature. A user wishing to query the chemical literature for a desired compound or molecule may provide the search tool with a reference to the desired compound or molecule (e.g., "hexane"). The search tool may transform the received reference into a corresponding reference using the standard notation for representing the desired compound or molecule. The search tool may then search the plurality of annotated chemical documents for the annotated reference. Based on the search, the search tool may identify one or more chemical documents that reference the desired compound or molecule.

In addition to identifying a specific chemical, a user may wish to find a class of chemicals with similar properties (e.g., all chemicals with multiple benzene rings). In one embodiment, the user provides the search tool with criteria describing desired chemical characteristics (e.g., "having multiple benzene rings"). The search tool may generate one or more regular expressions representing the received criteria (e.g., one or more regular expressions for the standard notation). The search tool may then search the plurality of annotated chemical documents for references to chemicals having the desired chemical characteristics.

In addition, a user may wish to identify chemicals not described in chemical literature (e.g., in a chemical drug discovery setting). In one embodiment, the user provides the search tool with criteria describing desired chemical characteristics (e.g., "having between two and four double-bonded oxygen atoms"). The criteria may specify desired chemical elements and, for each of the chemical elements, a desired amount of the respective chemical element, according to one embodiment. The criteria may describe a class of chemicals with similar properties. The search tool may also provide one or more mutation rules that specify desired mutation types. The mutation rules may be defined based on user input (e.g., from the user or from a different user). The search tool may generate one or more regular expressions based on the received criteria and the one or more mutation rules. The search tool may then determine one or more chemicals that satisfy the received criteria but that are not described in the chemical literature.

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

One embodiment of the invention is implemented as a program product for use with a computer system. The program(s) of the program product defines functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present invention, are embodiments of the present invention. Other media include communications media through which information is conveyed to a computer, such as through a computer or telephone network, including wireless communications networks. The latter embodiment specifically includes transmitting information to/from the Internet and other networks. Such communications media, when carrying computer-readable instructions that direct the functions of the present invention, are embodiments of the present invention. Broadly, computer-readable storage media and communications media may be referred to herein as computer-readable media.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

FIG. 1 is a block diagram illustrating a system 100 for searching chemicals described in chemical documents, according to one embodiment of the invention. The networked system 100 includes a computer 102. The computer 102 may be connected to other computers via a network 130. In general, the network 130 may be a telecommunications network and/or a wide area network (WAN). In a particular embodiment, the network 130 is the Internet.

The computer 102 generally includes a processor 104 connected via a bus 112 to a memory 106, a network interface device 110, a storage 108, an input device 114, and an output device 116. The computer 102 is generally under the control of an operating system (not shown). Examples of operating systems include UNIX, versions of the Microsoft Windows® operating system, and distributions of the Linux® operating system. (Note: Linux is at trademark of Linus Torvalds in the United States and other countries.) More generally, any operating system supporting the functions disclosed herein may be used. The processor 104 is included to be representative of a single CPU, multiple CPUs, a single CPU having multiple processing cores, and the like. Similarly, the memory 106 may be a random access memory. While the memory 106 is shown as a single entity, it should be understood that the memory 106 may comprise a plurality of modules, and that the memory 106 may exist at multiple levels, from high speed registers and caches to lower speed but larger DRAM chips. The network interface device 110 may be any type of network communications device allowing the computer 102 to communicate with other computers via the network 130.

The input device 114 may be any device for providing input to the computer 102. For example, a keyboard, keypad, light pen, touch-screen, track-ball, or speech recognition unit, audio/video player, and the like may be used. The output device 116 may be any device for providing output to a user of the computer 102. For example, the output device 116 may be any conventional display screen or set of speakers, along with their respective interface cards, i.e., video cards and sound cards (not shown). Although shown separately from the input device 114, the output device 116 and input device 114 may be combined. For example, a display screen with an integrated touch-screen, a display with an integrated keyboard, or a speech recognition unit combined with a text speech converter may be used.

The storage 108 may be a hard disk drive storage device. Although the storage 108 is shown as a single unit, the storage 108 may be a combination of fixed and/or removable storage devices, such as fixed disc drives, floppy disc drives, tape drives, removable memory cards, or optical storage. The memory 106 and the storage 108 may be part of one virtual address space spanning multiple primary and secondary storage devices.

As shown, the memory 106 of the computer 102 includes criteria 156, a search tool 150, and at least one regular expression 160. Further, the storage 108 of the computer 102 includes a plurality of chemical documents 152, a standard notation 153 for representing chemicals, a plurality of annotated chemical documents 154, and at least one mutation rule 158. FIGS. 2 through 7 and associated descriptions detail the structure and operation of the search tool 150 running on the computer 102.

In one embodiment, the search tool 150 identifies chemicals that are described in the documents 152 and that satisfy criteria 156 (e.g., from a user) specifying desired chemical characteristics. The search tool 150 may also identify at least one chemical document 152 that includes a reference to the identified chemicals. The search tool 150 may annotate the chemical documents 152 using a standard notation 153 for representing chemicals. For example, in one embodiment, the standard notation 153 may be the simplified molecular input line entry specification (SMILES) notation. SMILES is a line notation for encoding molecular structures. Of course, a variety of public or proprietary standards for representing chemicals may b used. The search tool may recognize chemicals expressed in a variety of different ways and then convert the recognized chemicals to a common language used by the search tool, according to one embodiment.

In one embodiment, the search tool 150 identifies (in the chemical documents 152) all references to chemicals (e.g., "hexane", "$C_6H_{14}$", "$CH_3(CH_2)_4CH_3$", etc.). The references may be expressed in distinct ways, e.g., via a scientific name (e.g., "sodium chloride"), molecular formula, structural formula, empirical formula (e.g., "NaCl"), other names (e.g., industrial/trade/household names, such as "common salt" or "table salt"), etc. The search tool 150 may annotate each reference with a standard notation 153 for representing the reference. For example, the SMILES notation may yield annotations of "[Na+]·[Cl−]" for sodium chloride and "CCCCCC" for hexane. That is, the search tool 150 may generate one or more associations between each reference to a chemical and the conversion to standard notation of the respective reference to the chemical.

The search tool 150 may identify one or more chemical documents 152 that reference a chemical specified by a user, according to one embodiment. For example, a user may input a chemical name or formula. The search tool 150 may convert the chemical name or formula into a standard notation. Alternatively, a user may input a chemical in the standard notation.

In one embodiment, the search tool 150 receives criteria 156 specifying desired chemical characteristics. For example, a researcher may input a set of criteria 156 that specify desired chemical characteristics. The search tool 150 may provide a user interface for receiving the criteria 156. An exemplary user interface screen is described below.

Figure 2:
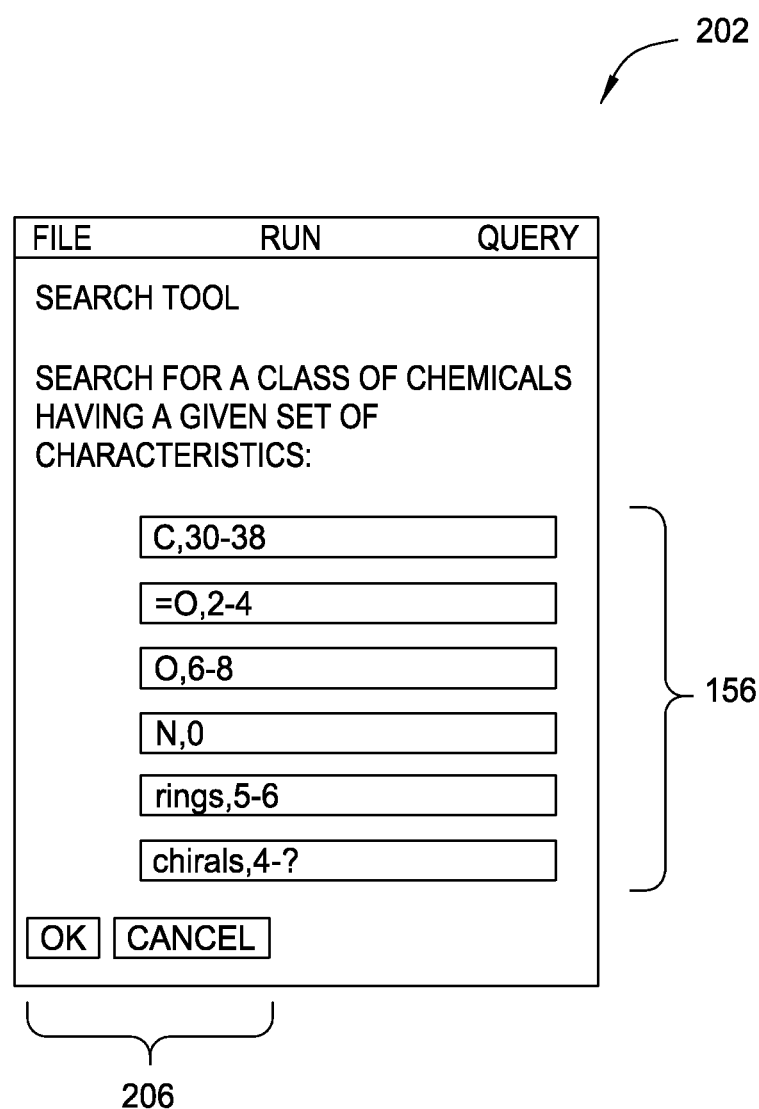
FIG. 2 illustrates a graphical user interface (GUI) screen for inputting criteria that specify desired chemical characteristics, according to one embodiment of the invention.

FIG. 2 illustrates a graphical user interface (GUI) screen 200 for inputting criteria 156 that specify desired chemical characteristics, according to one embodiment of the invention. As shown, the GUI screen 200 includes criteria 156 and buttons 206. The criteria 156 specify one or more desired chemical characteristics. The desired chemical characteristics include having thirty to thirty-eight carbon atoms (i.e., "C,30-38"), having two to four double-bonded oxygen atoms (i.e., "=O,2-4"), having six to eight oxygen atoms (i.e., "O,6-8"), having no nitrogen (i.e., "N,0"), having five or six carbon rings (i.e., "rings, 5-6"), and having 4 or more chiral centers (i.e., "chirals, 4-?"). The user may click on a button 206 labeled "OK" to submit the criteria 156 to the search tool 150, according to one embodiment. Alternatively, the user may click on a button 206 labeled "Cancel" to exit the GUI screen 200. Those skilled in the art will recognize that embodiments of the invention may be adapted to support other boolean operators (such as an "OR" operator) and other syntaxes for representing the criteria 156.

To assist a user in specifying the criteria 156, the search tool 150 may generate and display one or more "reference chemicals" to the user, according to one embodiment. The reference chemicals may be specified by the user. Exemplary reference chemicals are described below.

FIG. 3 illustrates GUI screens 300 for assisting a user in specifying the criteria 156, according to one embodiment of the invention. The GUI screens 300 include reference chemicals 302, 304, 306. In one embodiment, a user may specify a reference chemical (e.g., via chemical name or formula, etc.). The search tool 150 may generate and display the specified reference chemical to the user. The user may utilize the specified reference chemical as visual aids for identifying criteria 156 to input into the GUI screen 200. That is, the user may specify a known chemical having desired characteristics, and use a graphical representation of the known chemical as a visual aid for identifying and inputting desired characteristics of the chemical. In one embodiment, the search tool 150 may output the one or more reference chemicals 302, 304, 306 and the GUI screen 200 for simultaneous display to the user.

In one embodiment, the search tool 150 generates one or more regular expressions 160 based on the received criteria 156. Each regular expression 160 may be to be evaluated against the standard notation 153 (or more specifically, chemical references in the standard notation 153). As is known, a regular expression is a formal language for identifying strings of interest. An example of a standard for regular expressions is the IEEE (Institute of Electrical and Electronics Engineers) POSIX (Portable Operating System Interface for Unix) Extended Regular expressions (ERE) standard. For example, the ERE standard specifies the following syntax:

TABLE I

Syntax for regular expressions (ERE standard)

| | |
|---|---|
| . | Matches any single character |
| [ ] | Matches any single character contained in the brackets |
| [ ] | Matches any single character not contained in the brackets |
| ( ) | Defines a sub-regular expression |
| * | Matches the preceding element zero or more times. |
| {m,n} | Matches the preceding element at least m and not more than n times |

TABLE I-continued

Syntax for regular expressions (ERE standard)

| | |
|---|---|
| ? | Matches the preceding element zero or one time |
| + | Matches the preceding element one or more times |
| \| | Matches either the preceding element or the succeeding element |
| - | Specifies a range of characters between the preceding element and the succeeding element |

In Table I, an element may refer to a character or a subexpression. The following examples illustrate using the syntax of Table I. For example, "a.c" matches "aac", "abc", etc. Further, "[abcx-z]" matches "a", "b", "c", "x", "y", or "z". Further, "[^abc]" matches any character other than "a", "b", or "c". Further, "ab*c" matches "ac", "abc", "abbbc", etc. Further, "[xyz]*" matches "" (empty string), "x", "y", "z", "zx", "zyx", "xyzzy", etc. Further, "a{3,5}" matches "aaa", "aaaa", and "aaaaa". Further, "ba?" matches "b" or "ba". Further, "ba+" matches "ba", "baa", "baaa", etc. Further, "abc|def" matches "abc" or "def". Further, "(abc)+" matches "abc", "abcabc", "abcabcabc", etc. Further, "[^b]at" matches all strings matched by ".at" except "bat".

In one embodiment, each regular expression 160 may be to be evaluated against SMILES strings. That is, the search tool 150 may generate one or more regular expressions to represent the criteria 156 (e.g., having two to four double-bonded oxygen atoms (i.e., "=O,2-4"), having six to eight oxygen atoms (i.e., "O,6-8"), etc.). As an example, the search tool 150 may generate the following regular expressions to represent a chemical characteristic of "having one to three oxygen atoms": "[^O]*O[^O]*" (having one oxygen atom), "[^O]*O[^O]*O[^O]*" (having two oxygen atoms), and "[^O]*O[^O]*O[^O]*O[^O]*" (having three oxygen atoms). The generated regular expressions may also be combined using the "|" syntax of Table I. The search tool 150 may execute the generated regular expressions against the chemical documents 152 to identify chemicals satisfying the generated regular expressions, according to one embodiment. For example, a document may describe 2-Propanol, which has a SMILES string of "CC(O)C". The SMILES string satisfies the regular expression of "[^O]*O[^O]*" (having one oxygen atom). In executing the regular expression against a SMILES string for 2-Propanol described in the document, the search tool 150 may identify 2-Propanol as a chemical that satisfies the regular expression. The search tool 150 may also execute additional regular expressions against the SMILES string to determine whether the SMILES string satisfies other regular expressions generated from the criteria 156. If all regular expressions are satisfied, the search tool 150 may identify the SMILES string and/or the document as satisfying the criteria 156. For example, the search tool 150 may return the identified SMILES strings (or associated chemical name, etc.) and/or documents to a user.

In addition, the search tool 150 may, in various ways, improve efficiency of processing the regular expressions 160. For example, the search tool 150 may determine which of a plurality of regular expressions to process first that would eliminate the most results from a candidate result set (e.g., of chemicals and/or chemical documents 152). For instance, if far fewer compounds have four or more chiral centers than have six to eight oxygen atoms, the search tool 150 may execute a first regular expression for "having four or more chiral centers" against chemicals described in the documents. Further, the search tool 150 may execute a second regular expression for "having six to eight oxygen atoms" only against chemicals satisfying the first regular expression. That is, the search tool 150 may identify a desirable "weeder" regular expression and process the identified regular expression before processing other regular expressions.

The search tool 150 may identify a desirable "weeder" regular expression based on statistical data on chemicals, according to one embodiment. The statistical data may describe relative frequencies of chemical characteristics (e.g., having two double-bonded oxygen atoms) among chemicals described in the documents. The search tool 150 may query the statistical data to identify one or more "weeder" regular expressions (among the generated regular expressions). By identifying and applying a desirable "weeder" regular expression (prior to applying other regular expressions), the search tool 150 may reduce the number of regular expressions evaluated. Thus, the search tool 150 may process the regular expressions 160 more efficiently.

The search tool 150 may also improve efficiency of processing the regular expressions 160 by consolidating multiple regular expressions into a single regular expression, according to one embodiment. For example, search tool 150 may combine the regular expressions "[^O]*O[^O]*" (having one oxygen atom) and "[^O]*O[^O]*O[^O]*" (having two oxygen atoms) into "([^O]*O[^O]*)|( [^O]*O[^O]*O[^O]*)" (having one or two oxygen atoms).

While embodiments are described herein with reference to a search tool that generates and evaluates regular expressions, those skilled in the art will recognize that embodiments of the invention may be adapted to support formal languages and/or grammars other than regular expressions.

A user may wish to discover chemicals not described in the chemical documents 152. A chemical that is not described in a large number of chemical documents 152 (e.g., from chemical patent and chemical research paper repositories) may indicate that the chemical is yet unknown and/or undiscovered. In one embodiment, the search tool 150 explores a class of chemicals based on the criteria 156 and one or more mutation rules 158. The search tool 150 may iteratively apply the one or more mutation rules 158 to discover variants (or mutations) of chemicals. For each discovered variant, the search tool 150 may determine whether the respective discovered variant is described by the chemical documents 152. For example, if the discovered variant is not described by a chemical patent repository, the discovered variant may not yet be patented. Further, if the discovered variant is not described by a chemical research paper repository, the discovered variant may not yet be researched and/or known. For example, candidate drug formulas may be discovered.

Further, the search tool 150 may compute a score representing a commercial value of a chemical discovered by the search tool 150 but not referenced in the chemical documents 152, according to one embodiment. A "discovered chemical" refers to a chemical discovered by the search tool 150. The language "discovered" in "discovered chemical" refers only to discovery by the search tool 150. In other words, each discovered chemical may potentially be unpatented, unknown, and/or un-researched. The score may represent a commercial value of the discovered chemical. For example, the search tool 150 may compute a score for a discovered chemical based on determining a binding affinity of the discovered chemical to a desired receptor, determining whether the discovered chemical is chemically stable, etc. The binding affinity represents how likely the discovered chemical is to bind to the desired receptor.

Furthermore, the search tool 150 may perform molecular docking simulations only on those discovered chemicals having a computed score exceeding a predefined threshold score (or mark only those discovered chemicals for molecular docking). That is, the search tool 150 may identify, among a plurality of potentially unknown chemicals, a set of most promising chemicals (e.g., based on the computed score for each chemical). A chemical researcher may work on the most promising chemicals first. Embodiments of the invention may be adapted to support various ways of computing a score for a discovered chemical. For example, any in silico (computer) simulation technique may be applied to compute the score.

In one embodiment, the search tool 150 may perform the following process. The search tool 150 may generate one or more regular expressions based on both the received criteria 156 and the mutation rules 158. The mutation rules 158 specify ways in which the search tool 150 determines a next chemical to evaluate against a regular expression (i.e., from a search space of all possible chemicals, or all chemicals described in the documents). That is, the mutation rules 158 allow a user to hold any mutation process in line with design goals (i.e., to prevent the mutation process from being completely random). The mutation process may describe a genetic mutation from one class of chemicals to another. The mutation process may also describe any alteration from one chemical to another. Further, the mutation process may be integrated with external mutation algorithms (e.g., the search tool 150 may accept an external mutation component as a pluggable component).

Some well known examples of mutations include tautomerism, depurination, deamination, transition, transversion, etc. Tautomerism refers to a nucleotide base that is changed by the repositioning of a hydrogen atom, altering the hydrogen bonding pattern of that nucleotide base resulting in incorrect base pairing during replication. Depurination refers to a loss of a purine base to form an apurinic site. Deamination refers to hydrolysis changing a normal base to an atypical base containing a keto group in place of an original amine group. Transition refers to a purine changing to another purine (or a pyrimidine changing to another pyrimidine). Transversion refers to a purine becoming a pyrimidine (or vice versa). An example of deamination is changing cytosine to uracil, which may be represented by a mutation rule "C1=C(NC(=O)N=C1)N→C1=CNC(=O)NC1=O". That is, the mutation rules 158 specify how to mutate a SMILES string, according to one embodiment. In effect, the mutation rules 158 guide and/or prioritize chemicals evaluated next by the search tool 150 against the regular expressions 160. The mutation rules 158 may guide which regular expression is to be evaluated next, as well as which chemical is to be evaluated next (given a regular expression). In one embodiment, the mutation rules 158 may be represented as a mapping table between regular expressions. The mutation rules 158 may also be represented using formal grammars, such as a context-free grammar, according to one embodiment.

In one embodiment, the search tool 150 may discover, based on the generated regular expression 160 and the annotated chemical documents 154, one or more chemicals satisfying both the received criteria 156 and the mutation rules 158 (i.e., derived only by mutations satisfying the mutation rules 158), but that are not described in the chemical documents 150. The search tool 150 may recursively discover additional chemicals. For example, the search tool 150 may generate another set of regular expressions 160 using the received criteria 156 and the mutation rules 158. The number of iterations may be programmatically determined, user-specified, etc.

The search tool 150 evaluates the chemical strings generated following mutation. As noted above, each new class of chemicals may be represented as a regular expression. The search tool 150 may query the annotated chemical documents 154 using the regular expression generated during each round of mutation.

FIG. 4 illustrates a GUI output 400 of the search tool 150 of FIG. 1, according to one embodiment. As shown, the GUI output 400 includes information about iterations 404 of the mutation process, hits 406 in the annotated chemical documents 154, and regular expressions 160. As shown, each regular expression 160 results from a mutation, generated using the received criteria 156 and the mutation rules 158. Further, each regular expression 160 may represent a class of chemicals (e.g., with similar structural characteristics). For each regular expression 160, the search tool 150 determines a count of "hits" 406 of the regular expression 160 against the annotated chemical documents 154. For example, "one hit" represents that exactly one chemical document 152 references a chemical satisfying the associated regular expression 160. Further, "zero hits" represents that no chemical satisfying the associated regular expression 160 is referenced in any of the chemical documents 152.

Figure 5:
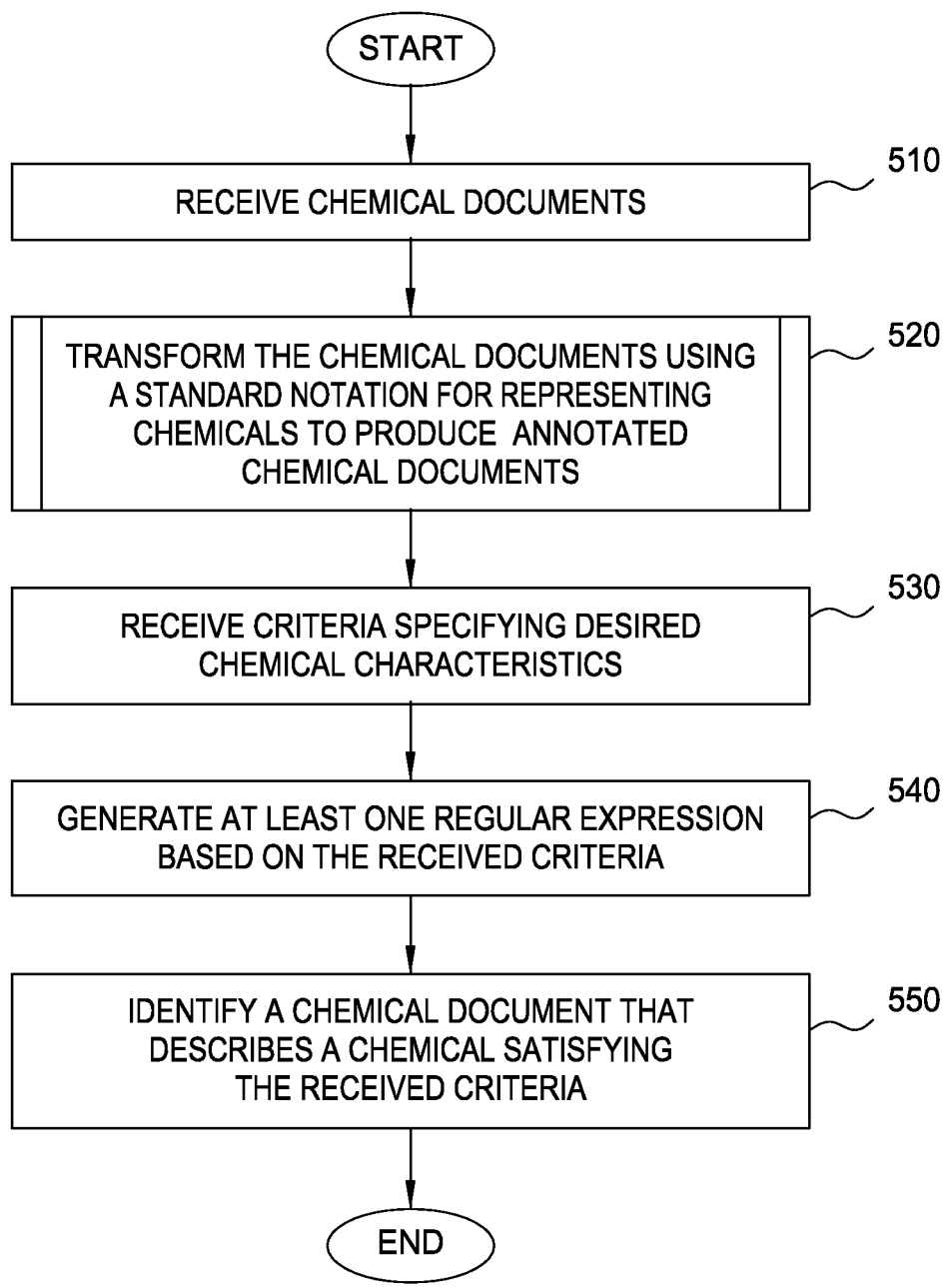
FIG. 5 is a flowchart depicting a method for searching chemicals referenced in documents, according to one embodiment of the invention.

FIG. 5 is a flowchart depicting a method 500 for searching chemicals described in chemical documents 152, according to one embodiment of the invention. The method 500 may be performed by the search tool 150 of FIG. 1. As shown, the method 500 begins at step 510, where the search tool 150 receives the chemical documents 152. For example, the search tool 150 may receive chemical patents and chemical research papers from one or more data repositories. At step 520, the search tool 150 converts the received chemical documents 152 using a standard notation 153 for representing chemicals to produce annotated chemical documents 154. For instance, each reference to a chemical (in a chemical patent or in a chemical research paper) may be transformed into a corresponding reference using the SMILES notation. Step 520 is further described below in conjunction with FIG. 8.

At step 530, the search tool 150 receives criteria 156 specifying characteristics of a described compound for the search tool 150 to search for, according to one embodiment. For example, a user may input a characteristic of "having two to four double-bonded oxygen atoms." At step 540, the search tool 150 generates at least one regular expression based on the criteria 156 received at step 530. For example, a regular expression may be generated for querying SMILES strings having two to four double-bonded oxygen atoms. At step 550, the search tool 150 identifies a chemical document that describes a chemical satisfying the received criteria. For example, a document may be identified that describes an organic compound containing two carbon-oxygen double bonds. After step 550, the method 500 terminates.

Figure 6:
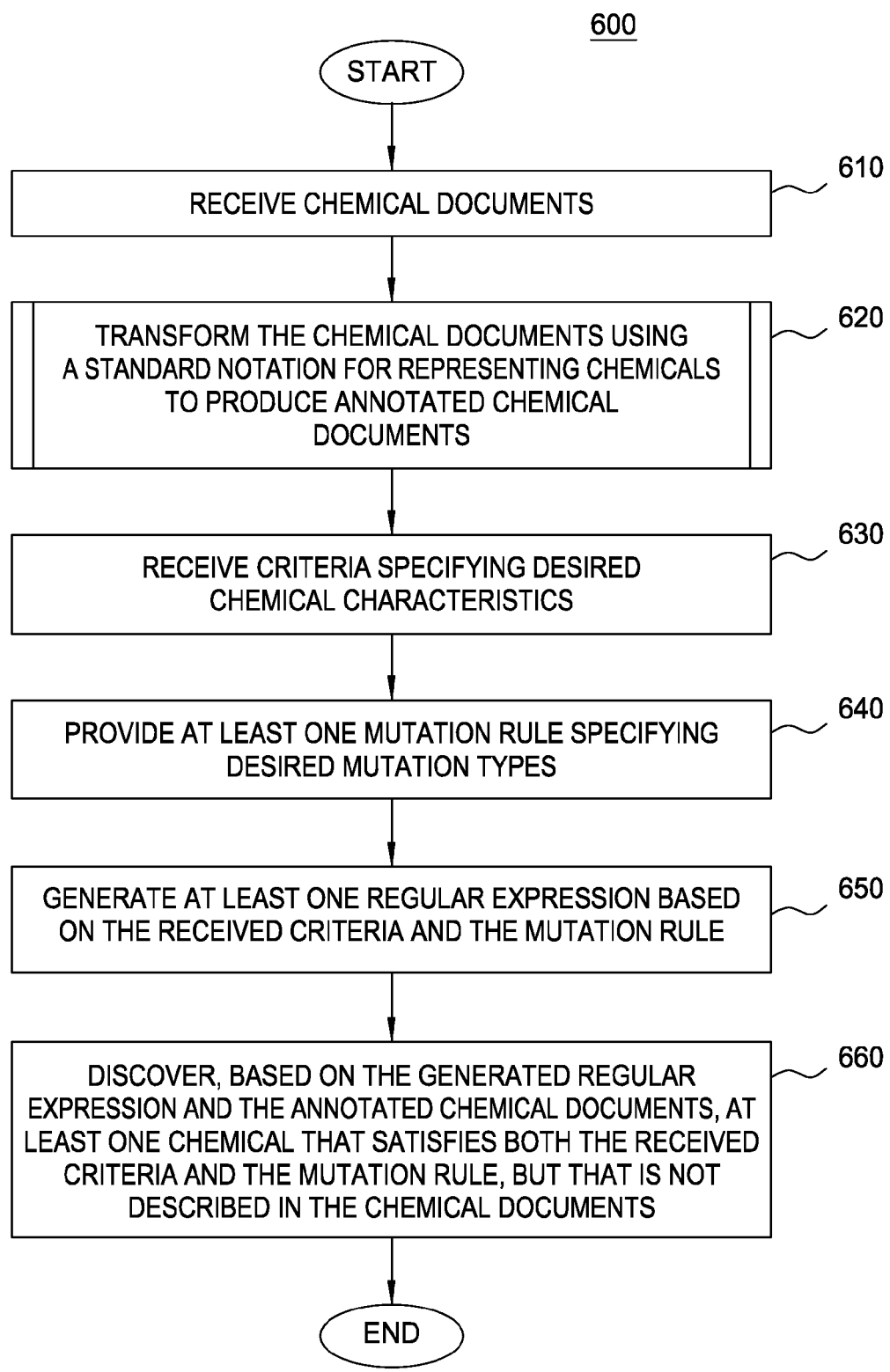
FIG. 6 is a flowchart depicting a method for discovering chemicals not referenced in chemical documents, according to one embodiment of the invention.

FIG. 6 is a flowchart depicting a method 600 for discovering chemicals not described in chemical documents 152, according to one embodiment of the invention. The method 600 may be performed by the search tool 150 of FIG. 1. As shown, the method 600 begins at step 610, where the search tool 150 receives the chemical documents 152. For example, the search tool 150 may receive chemical patents and chemical research papers from one or more data repositories. At step 620, the search tool 150 converts the received chemical documents 152 using a standard notation 153 for representing chemicals to produce annotated chemical documents 154. For example, each reference to a chemical (in a chemical patent or in a chemical research paper) may be transformed into a corresponding reference using the SMILES notation. Step 620 is further described below in conjunction with FIG. 8.

At step 630, the search tool 150 receives criteria 156 specifying desired chemical characteristics, according to one embodiment. For example, a user may input a desired chemical characteristic of "having four or more chiral centers." At step 640, the search tool 150 receives at least one mutation rule 158 specifying desired mutation types. For example, the mutation rule 158 may specify to increase the number of hydrogen atoms, carbon atoms, or oxygen atoms by at most, one through each iteration of the mutation process. At step 650, the search tool 150 generates at least one regular expression 160 based on the received criteria 156 and the mutation rule 158. For example, a regular expression may be generated for querying SMILES strings having four or more chiral centers.

At step 660, the search tool 150 may discover, based on the generated regular expression 160 and the annotated chemical documents 154, at least one chemical that satisfies both the received criteria 156 and the mutation rule 158, but that is not described in the chemical documents 154. For example, an organic compound may be identified that has four chiral centers and that satisfies the mutation rule 158 but that is not described by the chemical documents 152. In one embodiment, the method 600 may return to step 650 to generate a new regular expression based on the mutation rule 158. After step 660, the method 600 terminates.

Figure 7:
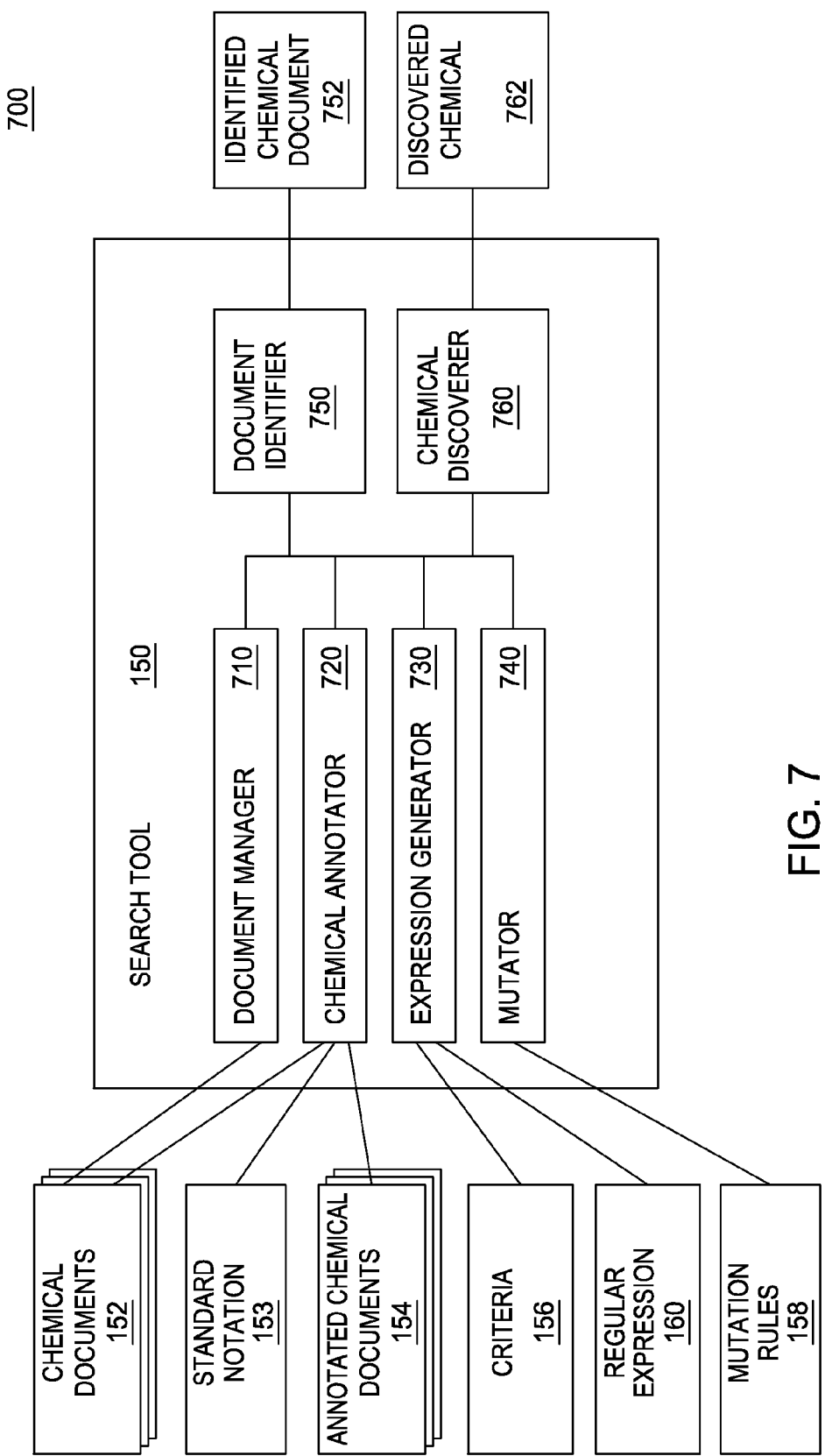
FIG. 7 is a block diagram illustrating components of a search tool, according to one embodiment of the invention.

FIG. 7 is a block diagram illustrating components 700 of the search tool 150 of FIG. 1, according to one embodiment of the invention. As shown, the search tool 150 includes a document manager 710, a chemical annotator 720, a regular expression generator 730, a mutator 740, a document identifier 750, and a chemical discoverer 760.

In one embodiment, the document manager 710 receives the chemical documents 152. For example, the document manager 710 may receive chemical patents and chemical research papers from one or more data repositories. The chemical annotator 720 annotates the chemical documents 152 according to the standard notation 153 to produce annotated chemical documents 154, according to one embodiment. For example, the chemical annotator 720 may annotate chemical references in the chemical patents and chemical research papers with SMILES strings representing the references.

The regular expression generator 730 creates a regular expression 170 based on the criteria 156, according to one embodiment. For example, the regular expression generator 730 may generate a regular expression against SMILE strings, based on a criterion of "having more than thirty carbon atoms." The document identifier 750 identifies a chemical document 752 (of the chemical documents 152) that references a chemical satisfying the generated regular expression 160, according to one embodiment. For example, the document identifier 750 may identify a chemical research report that describes a chemical satisfying the regular expression.

The mutator 740 receives one or more mutation rules 158 and performs mutations on chemicals (or specifically, representations thereof) to generate new chemicals based on the mutation rules 158, according to one embodiment. For example, a mutator 740 may generate a new chemical by increasing the number of carbon and hydrogen atoms of an organic compound. The chemical discoverer 760 finds new chemicals 762 that satisfy the received criteria 156 and the mutation rules 158, but that are not described in the chemical documents 152, according to one embodiment. For example, the chemical discoverer 760 may find an organic compound that has more than thirty carbon atoms, that has been mutated only by increasing the number of carbon and hydrogen atoms, and that is not described in any of the chemical documents 152.

Figure 8:
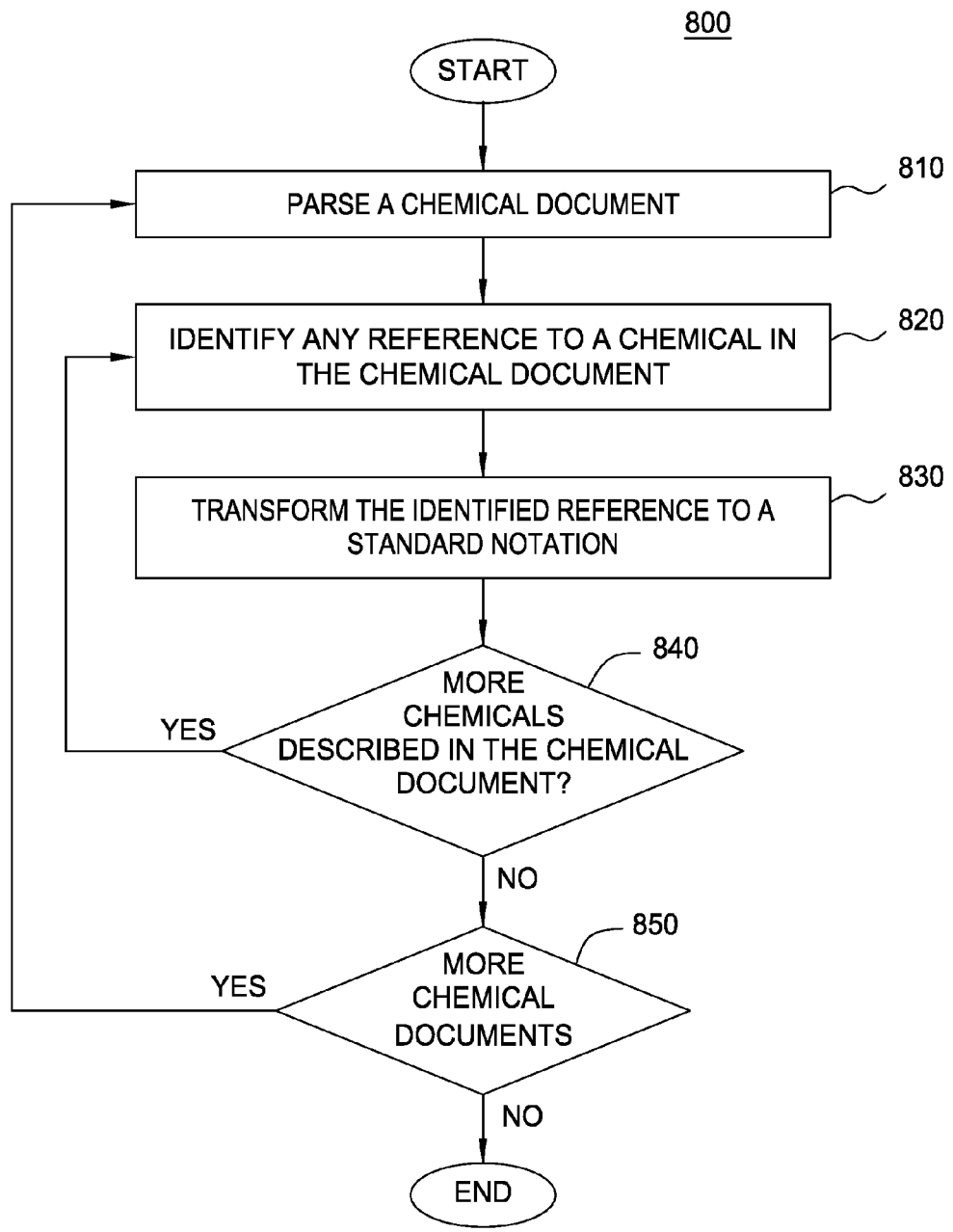
FIG. 8 is a flowchart depicting a method for transforming data representing chemical and/or molecular compounds referenced in a collection of documents, according to one embodiment of the invention.

FIG. 8 is a flowchart depicting a method for transforming data representing chemical and/or molecular compounds described in a document, according to one embodiment of the invention. The method 600 may be performed by the search tool 150 of FIG. 1. Further, the method 800 corresponds to step 520 of FIG. 5 and to step 620 of FIG. 6. As shown, the method 800 begins at step 810, where the search tool 150 parses a chemical document 152. At step 820, the search tool 150 identifies any reference to a chemical in the chemical document 152. For example, the search tool 150 may identify a reference to hexane, regardless of a form or format in which the reference appears in the chemical document (e.g., "hexane", C6H14 (i.e., a molecular formula for hexane), CH3CH2CH2CH2CH2CH3 (a structural formula for hexane), CH3(CH2)4CH3 (a structural formula for hexane), or C3H7 (an empirical formula for hexane)).

At step 830, the search tool 150 transforms the identified reference into a corresponding reference using a standard notation. For example, the search tool 150 may transform C6H14 (i.e., a molecular formula for hexane) to CCCCCC (i.e., the SMILES string for hexane). In one embodiment, the search tool 150 may annotate the identified reference with the transformed reference. In another embodiment, the search tool 150 may annotate a chemical index to the chemical documents with the transformed reference.

At step 840, the search tool 150 determines whether more chemicals are described in the chemical document 152. If so, the method 800 returns to step 820 to identify a next reference. Otherwise, the search tool 150 determines whether more chemical documents 152 remain to be evaluated (step 850). If so, the method 800 returns to step 810 to parse a next chemical document 152. Otherwise, the method 800 terminates.

Of course, the embodiments described herein are intended to be illustrative and not limiting of the invention, and other embodiments are broadly contemplated. Those skilled in the art will recognize, for example, that embodiments of the invention may be adapted to support other criteria, regular expressions, documents, notations, and mutation rules.

Advantageously, embodiments of the invention search chemicals described in chemical documents. In one embodiment, a search tool may receive the chemical documents. The search tool may annotate the chemical documents using a standard annotation for representing chemicals to produce a plurality of annotated chemical documents. The search tool may also receive criteria specifying desired chemical characteristics. The search tool may generate at least one regular expression based on the received criteria. The search tool may identify, based on the search and of the chemical documents, a chemical document that describes a chemical satisfying the received criteria. Further, the search tool may generate the at least one regular expression based on the received criteria and a received mutation rule. The search tool may also discover, based on the generated regular expression and the annotated chemical documents, a chemical that satisfies both the received criteria and the received mutation rule, but that is not described in the chemical documents.

While the foregoing is directed to embodiments of the present invention, other and further embodiments of the invention may be devised without departing from the basic scope thereof, and the scope thereof is determined by the claims that follow.

What is claimed is:

1. A computer-implemented method to use regular expressions to identify chemical compounds matching specified criteria, comprising:

configuring one or more computer processors to perform an operation for searching a plurality of documents which include references to chemical compounds, wherein the references to chemical compounds express the chemical compounds using a plurality of different formats, comprising:
  receiving the plurality of documents;
  receiving the criteria specifying desired chemical characteristics;
  generating at least one regular expression based on the received criteria;
  evaluating, by operation of the one or more computer processors, chemical compounds referenced in the plurality of documents against the at least one regular expression to identify one or more of the plurality of documents satisfy the received criteria.

2. The computer-implemented method of claim 1, wherein the operation further comprises:
  parsing each of the plurality of documents to identify references to chemical compounds; and
  transforming each of the identified references into a corresponding reference using the standard notation.

3. The computer-implemented method of claim 2, wherein the transformed references are evaluated against the regular expression.

4. The computer-implemented method of claim 1, wherein the standard notation comprises a simplified molecular input line entry specification (SMILES) notation and wherein each of the plurality of documents is selected from at least a chemical patent, a chemical research paper, and a chemical lab experiment document, wherein the plurality of different formats includes a molecular formula, a structural formula, an empirical formula, an industrial name, a trade name, and a household name;
  wherein the references to chemical compounds include a first chemical compound expressed using the molecular formula, a second chemical compound expressed using the structural formula, a third chemical compound expressed using the empirical formula, a fourth chemical compound expressed in terms of the industrial name, a fifth chemical compound expressed in terms of the trade name, and a sixth chemical compound expressed in terms of the household name.

5. The computer-implemented method of claim 1, wherein the desired chemical characteristics specify a plurality of desired chemical elements and, for each of the chemical elements, a desired amount of the respective chemical element.

6. A computer readable storage medium containing a program which, when executed, performs an operation for searching a plurality of documents which include references to chemical compounds, wherein the references to chemical compounds express the chemical compounds using a plurality of different formats, comprising:
  receiving the plurality of documents;
  receiving criteria specifying desired chemical characteristics;
  generating at least one regular expression based on the received criteria;
  evaluating chemical compounds referenced in the plurality of documents against the at least one regular expression to identify one or more of the plurality of documents that reference a chemical compound satisfying the received criteria.

7. The computer readable storage medium of claim 6, wherein the operation further comprises:
  parsing each of the plurality of documents to identify references to chemical compounds; and
  transforming each of the identified references into a corresponding reference using the standard notation.

8. The computer readable storage medium of claim 7, wherein the transformed references are evaluated against the regular expression.

9. The computer readable storage medium of claim 6, wherein the standard notation is the simplified molecular input line entry specification (SMILES) notation and wherein each of the plurality of documents is selected from at least a chemical patent, a chemical research paper, and a chemical lab experiment document, wherein the plurality of different formats includes a molecular formula, a structural formula, an empirical formula, an industrial name, a trade name, and a household name;
  wherein the references to chemical compounds include a first chemical compound expressed using the molecular formula, a second chemical compound expressed using the structural formula, a third chemical compound expressed using the empirical formula, a fourth chemical compound expressed in terms of the industrial name, a fifth chemical compound expressed in terms of the trade name, and a sixth chemical compound expressed in terms of the household name.

10. The computer readable storage medium of claim 6, wherein the desired chemical characteristics specify a plurality of desired chemical elements and, for each of the chemical elements, a desired amount of the respective chemical element.

11. A system, comprising:
  a computer processor; and
  a memory containing a program, which when executed by the processor is configured to perform an operation for searching a plurality of documents which include references to chemical compounds, wherein the references to chemical compounds express the chemical compounds using a plurality of different formats, the operation comprising:
    receiving the plurality of documents;
    receiving criteria specifying desired chemical characteristics;
    generating at least one regular expression based on the received criteria;
    evaluating, by operation of the computer processor, chemical compounds referenced in the plurality of documents against the at least one regular expression to identify one or more of the plurality of documents that reference a chemical compound satisfying the received criteria.

12. The system of claim 11, wherein the operation further comprises:
  parsing each of the plurality of documents to identify references to chemical compounds; and
  transforming each of the identified references into a corresponding reference using the standard notation.

13. The system of claim 12, wherein the transformed references are evaluated against the regular expression.

14. The system of claim 11, wherein the standard notation is the simplified molecular input line entry specification (SMILES) notation and wherein each of the plurality of documents is selected from at least a chemical patent, a chemical research paper, and a chemical lab experiment document, wherein the plurality of different formats includes a molecular formula, a structural formula, an empirical formula, an industrial name, a trade name, and a household name;

wherein the references to chemical compounds include a first chemical compound expressed using the molecular formula, a second chemical compound expressed using the structural formula, a third chemical compound expressed using the empirical formula, a fourth chemical compound expressed in terms of the industrial name, a fifth chemical compound expressed in terms of the trade name, and a sixth chemical compound expressed in terms of the household name.

15. The system of claim 11, wherein the desired chemical characteristics specify a plurality of desired chemical elements and, for each of the chemical elements, a desired amount of the respective chemical element.

\* \* \* \* \*